United States Patent [19]

Ferrari

[11] E Re. 30,555

[45] Reissued Mar. 24, 1981

[54] METHOD OF PRODUCING STRING OF POLYAMIDE AND STRINGED RACKETS WITH SUCH STRING

[76] Inventor: Harry Ferrari, 144 W. Swissvale Ave., Pittsburgh, Pa. 15218

[21] Appl. No.: 92,359

[22] Filed: Nov. 8, 1979

Related U.S. Patent Documents

Reissue of:

[64] Patent No.: 4,015,133
Issued: Mar. 29, 1977
Appl. No.: 656,808
Filed: Feb. 10, 1976

U.S. Applications:

[63] Continuation-in-part of Ser. No. 540,794, Jan. 14, 1975, abandoned.

[51] Int. Cl.[3] ..... A61K 27/02

[52] U.S. Cl. ..... 250/492 R; 204/159.19

[58] Field of Search ..... 250/492 R, 492 B, 493; 204/155, 156, 157.1 R, 157.11, 164, 159.15, 159.19

[56] References Cited

U.S. PATENT DOCUMENTS

| | | | |
|---|---|---|---|
| 2,257,177 | 9/1941 | Luster | 204/156 |
| 2,878,174 | 3/1959 | Rainer et al. | 250/492 |
| 3,069,283 | 12/1962 | Coleman | 204/164 |
| 3,842,705 | 10/1974 | Woodard et al. | 204/159.19 |
| 4,043,555 | 8/1977 | Conn | 204/159.19 |

*Primary Examiner*—David C. Nelms
*Attorney, Agent, or Firm*—Hymen Diamond

[57] ABSTRACT

String of polyamide is irradiated with dosages of $10^4$ to $10^{10}$ rads. It has been discovered by actual experience that in string which is treated in this way the cross linkage of the molecules is enhanced. Such string has higher elasticity and substantially lower damping when set into oscillation than untreated string and that a tennis racket produced with such string is superior to a racket with untreated polyamide string. The dosage is not so high as to cause the string to become brittle.

7 Claims, 3 Drawing Figures

METHOD OF PRODUCING STRING OF POLYAMIDE AND STRINGED RACKETS WITH SUCH STRING

Matter enclosed in heavy brackets [ ] appears in the original patent but forms no part of this reissue specification; matter printed in italics indicates the additions made by reissue.

REFERENCE TO RELATED DOCUMENTS

1. This application is a continuation-in-part of U.S. Pat. application Ser. No. 540,794, filed Jan. 14, 1975 to Harry Ferrari for METHOD OF PRODUCING STRING OR POLYAMIDE AND STRINGED RACKETS AND STRINGED MUSICAL INSTRUMENTS WITH SUCH STRINGS now abandoned.

2. The Use of Plastics and Elastometers in Nuclear Radiation—W. W. Parkinson and O. Sisman—Nuclear Engineering and Design 17(1971) pgs. 247-280 particularly pg. 269—Published by North Holland Publishing Co.

3. Strength of Irradiated Drawn and Undrawn Nylon—Hsiao, Y. C. Da, A. Haynes—British Journal of Applied Physics Vol. II July 1960 pgs. 277-279.

BACKGROUND OF THE INVENTION

This invention relates to [stringed apparatus such as] stringed rackets [and stringed instruments] and has particular relationship to the strings forming a part of such [apparatus] *rackets*. [The expression stringed apparatus as used in this application means stringed rackets and stringed instruments and other devices to which this invention is applicable. To a large extent this] *This* application is confined to stringed rackets [both in the interest of concreteness and also] because the remarkable results which gave rise to this invention have been experienced with rackets. [Since the string according to this invention has properties which are advantageous in stringed musical instruments as well as stringed rackets, musical instruments as well as rackets are within the scope of this invention.]

In accordance with the teachings of the prior art, string for stringed rackets are made of animal gut, polymer materials such as polyamide which is sold under the name NYLON, or metals such as steel. Gut is considered to be superior for stringed rackets from the standpoint of the advantage which its use gives to the player. The principal advantage of gut is that it operates with less internal damping than other materials, and the ball rebounds harder and with less loss of energy on impact. Essentially damping is a measure of resilience; when the damping is low, the resilience is high and when the damping is high, the resilience is low. Gut has high resilience. However, gut is high in cost, variable in quality, has only modest strength, has low durability, and is unable to withstand for any length of time high moisture or humid environments. The above disadvantages have limited the use of gut to players who are willing to sacrifice high cost and relatively high probability of failure for better playing characteristics. Polyamides have good durability and good resistance to water or dampness. However, they lack the low damping of gut.

Steel has found limited use because it transfers the numerous impacts of the ball to the frame substantially undamped and is damaging to the frame particularly if it is made of materials other than steel. Steel is also damaging to tennis balls resulting in excessive wear and low life.

[A wide variety of materials have been used for strings of musical instruments such as gut, steel, polymers such as polyamides, aluminum, composites such as steel—or aluminum-wound gut or polyamide. The exact material selected depends on the instrument and tonal qualities desired for any particular string. Normally, to achieve lower notes, the density of the strings is increased, for example, steel-wound gut or polyamide is used; and the tension on the string is reduced.]

It is an object of this invention to overcome the above disadvantages of the prior art and to provide string of polyamide having low internal damping for stringed [apparatus] *rackets*. It is another object of this invention to provide improved stringed [apparatus] *rackets* of which polyamide string having low internal damping shall form a part.

SUMMARY OF THE INVENTION

This invention arises from the discovery that by irradiating polyamide with elementary particles which inject energy into its molecular structure its internal damping is reduced. In addition, it has been discovered that the elasticity of polyamides is increased. The irradiation may be produced by electrons, neutrons, gamma rays, protons, alpha particles, X-rays or other particles or combinations of these particles. The radiation dosage should be between $10^4$ and $10^{10}$ rads. A rad is the quality of radiation which leads to the absorption of 100 ergs of energy per gram of irradiated material.

In accordance with this invention the polyamide string is drawn and reeled and progressively irradiated as it passes from the feed reel to a take-up reel. The string as it is irradiated moves at a speed of about 240 feet per second. The tension impressed on the string is small but sufficient to enable the take-up reel to wind the string at the desired speed. Typically the string has diameter of about 0.055 inch and the tensional force is 5 to 10 pounds. The tension is pounds-per-square inch is the force divided by the cross-sectional area of the string, that is, typically $5/\pi(0.0275)^2$ to $10/\pi(0.0275)^2$. The irradiation at $10^4$ to $10^{10}$ rads takes place at room temperature and pressure; that is, at about 70° F. and about 14.7 pounds per square inch. The dosage of the radiation and not the dose rate is important in producing the desired improvement. The dosage is measured in rads.

The string so treated is then used in [stringed apparatus such as] stringed rackets. [or stringed musical instruments.] Actual experience with a tennis racket strung with polyamide string irradiated with dosages of between $10^4$ and $10^{10}$ rads has revealed that the racket in play functions like a racket strung with gut string as far as the damping factor is concerned. In addition, because the elasticity of the string is increased the control of the ball is improved. It is to be noted that because the damping is low, the high elasticity does not militate against effective elastic rebound of the ball from the racket.

In polymers such as polyamide, radiation produces competing reactions, scission or cleavage and cross linking depending on the dosage of radiation, temperature environment and other conditions. The cleavage reaction, which predominates at low irradiation doses, results in the breakdown of the long polymer chains into smaller chains. The cross-linking reaction, which predominates at high irradiation doses, results in the binding together of molecules of the polymer into a network structure. At intermediate doses there is a mixture of the two reactions. Cleavage normally results in a decrease in tensile strength and modulus of elasticity, whereas cross-linking increases both the tensile strength and the modulus of elasticity. If the dosage is excessive, complete cross-linkage may take place but the string becomes brittle. It is desirable that the dosage be such as to enhance the cross-linkage without producing brittle string.

The optimum irradiation dose to be used depends on many factors such as the specific polyamide used, string thickness, irradiation environment (atmosphere and temperature), etc., and the intended end use of the product; however, it should normally vary between $10^4$ and 10 rads at the room temperature and pressure. The irradiation can be achieved by any of the particles listed above.

Strings produced in the practice of this invention are applicable to any stringed rackets including tennis, badminton, squash and paddle-ball rackets. [and to other sports equipment such as backboards for baseball, tennis, etc. The invention is also useful for improving the resilience of fishing lines as desired.]

[Another application for irradiated strings is for stringed musical instruments as mentioned. The irradiation studies conducted on polyamide strings for stringed rackets reveal that irradiation under the proper conditions improve the mechanical properties of strings for stringed musical instruments, thereby greatly increasing their value or alternatively broadening the flexibility by which they may be used.]

For a better understanding of this invention both as to its organization and as to its method of operation, together with additional objects and advantages thereof, reference is made to the following description, taken in conjunction with the accompanying drawing, in which:

*FIG. 2 shows a racket* stringed apparatus including strings produced in the practice of this invention; and FIG. [4] *3* is a graph illustrating an advantage achieved in the practice of this invention.

Figure 1:
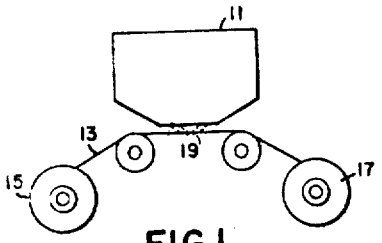
FIG. 1 is a diagrammatic view of apparatus for practicing this invention.

The apparatus shown in FIG. 1 includes a generator 11 of elementary particles, for example, an electron-beam generator. The generator 11 is of the type which emits its particles into the atmosphere. The polyamide to be irradiated is formed into string 13 and wound on a feed reel 15. Usually the string is formed of a plurality of threads [would] *wound* or twisted together and usually coated with anti-wear coating. The string 13 is fed from the feed reel 15 to the take-up reel 17 through a beam 19 of the particles. The energy of the beam 19 is so related to the speed of the string 13 that the energy of the particles impinging on the string 13 is adequate to provide the required rad dosage. For example, where the beam 19 is an electron beam the dosage is set by setting the beam current and the beam voltage.

Typically, a polyamide string of 0.055 inch diameter was irradiated with $10^7$ rads at about 70° F. and about 14.7 pounds per square inch pressure. The mechanical properties of the string before and after irradiation is shown in the following Table I:

TABLE 1

| Property | Unirradiated | Irradiated |
|---|---|---|
| Yield Strength | 55,000 psi | 54,200 psi |
| Tensile Strength | 73,400 psi | 73,000 psi |

TABLE 1-continued

| Property | Unirradiated | Irradiated |
|---|---|---|
| Modulus of Elasticity | $0.32 \times 10^6$ psi | $0.275 \times 10^6$ psi |
| Elongation | 36% | 33.1% |

The significant data is the modulus of elasticity. The effect of the radiation is to decrease the modulus from $0.32 \times 10^6$ to $0.275 \times 10^6$. The modulus is defined as the change in stress $\sigma$ divided by the corresponding strain produced. Within the elastic limit the stressstrain curve is nearly linear and the modulus, being the slope, is constant. In FIG. [4] *3* stress $\sigma$ is plotted vertically and strain horizontally. The curve 21 for the treated string has a smaller slope than the curve 23 for the untreated string. It is seen that for the same change, $\Delta\sigma$, in stress the string of the lower modulus produces a higher strain than the string with the higher modulus. The treated string with the lower modulus is more elastic, and therefore in the case of tennis strings will follow the ball better than untreated string which results in improved control over the ball.

However, the improved elasticity [along] *alone* is not adequate to produce a satisfactory string *for a racket*. The resiliency must also be increased which means that the internal damping or loss coefficient must be reduced. The loss coefficient is the decrement or the decrease in the vibration amplitude which occurs as a string vibrates after it is set into vibration. Essentially the loss coefficient determines the Q of the string and is high for low-loss coefficient and low for high-loss coefficient.

Table II below shows the improvement achieved in loss coefficient in polyamide string of 0.055 diameter by irradiation with a dosage of $10^7$ rads at about 70° F. and about 14.7 pounds per square inch pressure.

TABLE II

| | Loss Coefficient | | |
|---|---|---|---|
| Preload-Pounds | Unirradiated | Irradiated | % Improvement |
| 40 | 9% | 7% | 22 |
| 60 | 14% | 11% | 21 |
| 80 | 16% | 12% | 25 |

All data in Table II are an average of 4 measurements

To produce this table unirradiated and irradiated string of 0.055 inch diameter were subjected to tension by applying the forces shown in the left-hand column. The string was vibrated and the decrease in amplitude of the vibration per cycle was measured. The irradiated string (third column from left) manifested a substantially lower loss coefficient than the unirradiated string (second column). The net result is that the irradiated string has a harder rebound impact on the ball than unirradiated string.

Figure 2:
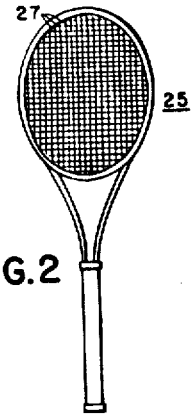
[FIGS. 2 and 3 show]
Figure 3:
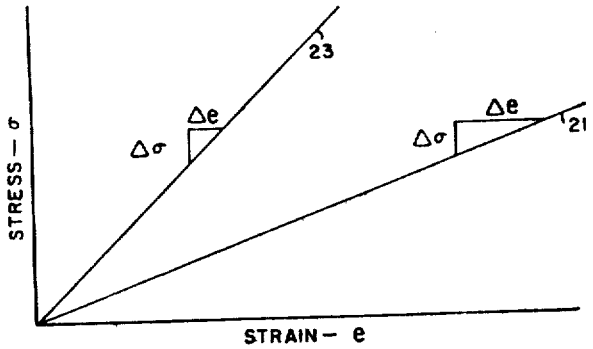

FIG. 2 shows a tennis racket 25 with treated polyamide string 27 in accordance with this invention. Such a racket was found by actual use to be superior to a racket with untreated polyamide in its sharp and precise reflection of the ball. [FIG. 3 shows a musical instrument 29 with string 31 according to this invention.]

While preferred practice of this invention is disclosed herein, many modifications thereof are feasible. This invention is not to be restricted except insofar as is necessitated by the spirit of the prior art.

I claim:

1. The method of substantially improving [the elasticity and decreasing and damping of] *stringed rackets having* string composed of polyamide [for stringed apparatus] which comprises *improving the elasticity and decreasing the damping of said string by* irradiating the string with [radition] *radiation*, the magnitude of the energy of said radiation being in the range between the energy for which cleavage is predominately produced and the energy for which linkage alone is produced, so that a decrease in the modulus of elasticity of the treated string is accompanied by a decrease in the damping loss coefficient of the treated string.

2. The method of claim 1 wherein the string is formed prior to its exposure to radiation and thereafter is irradiated progressively by being drawn through a beam of radiation.

3. The method of claim 1 wherein the string is irradiated with a dosage of $10^4$ to $10^{10}$ rads.

4. A string for stringed [apparatus] *rackets* having improved elasticity *and* reduced damping loss composed of polyamide irradiated with radiation, the magnitude of the energy of said radiation being in the range between the energy for which cleavage is predominately produced and the energy for which cross linkage alone is produced, so that a decrease in the modulus of elasticity of the treated string is accompanied by a decrease in the damping-loss coefficient of the treated string.

5. A stringed racket whose strings are composed of the strings of claim 4.

[6. A stringed instrument at least one of whose strings is composed of the string of claim 4.]

[7. A string of polyamide for stringed apparatus the cross linkage of whose molecular chains is enhanced.]

*8. Strings for a stringed racket, said racket having tensioned synthetic strings with resilience similar to natural gut, said strings being produced by providing a filament of a polyamide material and irradiating the filament with a radiation dosage of about* $10^4$ to $10^{10}$ rads, thereby causing cross linking of molecules and increasing the resilience of said filament.

*9. A stringed racket whose string is composed of the string of claim 8.*

* * * * *